United States Patent
Pifer et al.

(10) Patent No.: US 10,080,854 B1
(45) Date of Patent: Sep. 25, 2018

(54) SUCTION CATHETER WITH INTUBATION GUIDE STYLET

(71) Applicants: Douglas R. Pifer, Dunedin, FL (US); Gregory A. Pifer, Valrico, FL (US)

(72) Inventors: Douglas R. Pifer, Dunedin, FL (US); Gregory A. Pifer, Valrico, FL (US)

(*) Notice: Subject to any disclaimer, the term of this patent is extended or adjusted under 35 U.S.C. 154(b) by 550 days.

(21) Appl. No.: 14/505,646

(22) Filed: Oct. 3, 2014

(51) Int. Cl.
*A61M 16/04* (2006.01)

(52) U.S. Cl.
CPC ........ *A61M 16/0463* (2013.01); *A61M 16/04* (2013.01); *A61M 16/0465* (2013.01); *A61M 16/0488* (2013.01)

(58) Field of Classification Search
CPC ...... A61M 16/0477–16/0484; A61M 16/0486; A61M 16/0488; A61M 16/0463; A61M 2025/1056
See application file for complete search history.

(56) References Cited

U.S. PATENT DOCUMENTS

| | | | | |
|---|---|---|---|---|
| 4,244,362 A | * | 1/1981 | Anderson | A61M 16/04 128/200.26 |
| 4,699,138 A | * | 10/1987 | Behrstock | A61M 16/0463 128/207.16 |
| 5,372,131 A | * | 12/1994 | Heinen, Jr. | A61M 16/04 128/200.26 |
| 5,733,242 A | * | 3/1998 | Rayburn | A61B 1/0052 600/120 |
| 2007/0227543 A1 | * | 10/2007 | Peichel | A61M 25/00 128/207.14 |
| 2009/0071484 A1 | * | 3/2009 | Black | A61M 16/0484 128/207.14 |
| 2011/0023871 A1 | * | 2/2011 | Pacey | A61M 16/04 128/200.26 |
| 2013/0035548 A1 | * | 2/2013 | Ianchulev | A61B 1/00052 600/120 |
| 2016/0262603 A1 | * | 9/2016 | Molnar | A61B 1/267 |

* cited by examiner

*Primary Examiner* — Valerie L Woodward

(57) ABSTRACT

A suction device has an upper section with an upper end formed as a handle and a lower end shaped as a torus. A lateral component is integrally formed with the suction device and extends from adjacent to the upper end and adjacent to the lower end. The lateral component has a passageway there through. The suction device and the lateral component are fabricated of a generally rigid plastic material. An intubation guide stylet is slidably positioned in the passageway of the lateral component. The top of the intubation guide stylet is positionable above the lateral component and the bottom is positionable below the lateral component.

3 Claims, 3 Drawing Sheets

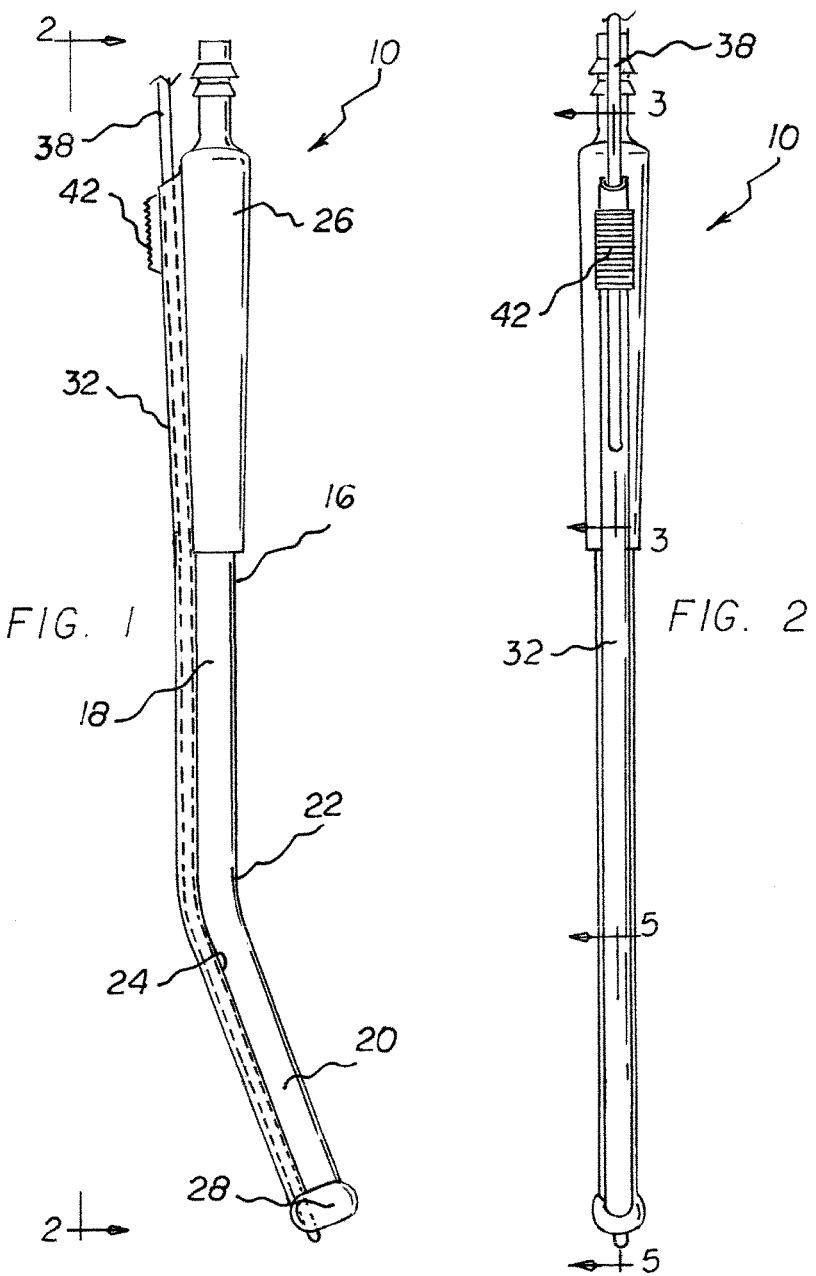

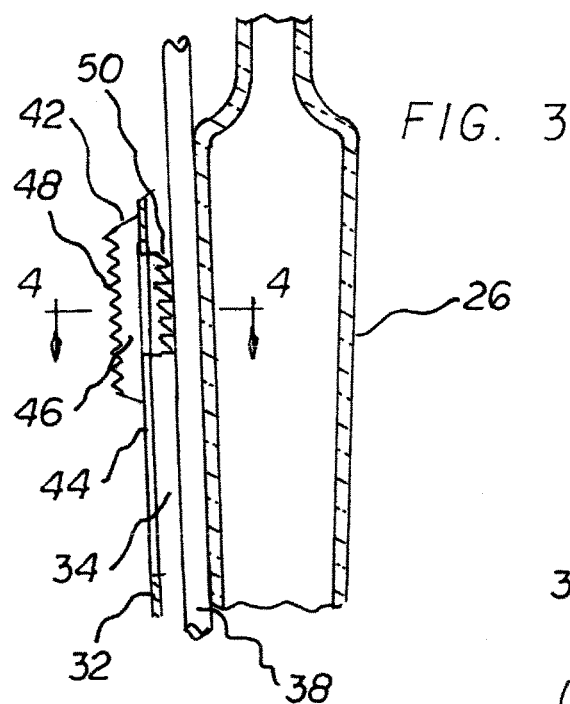
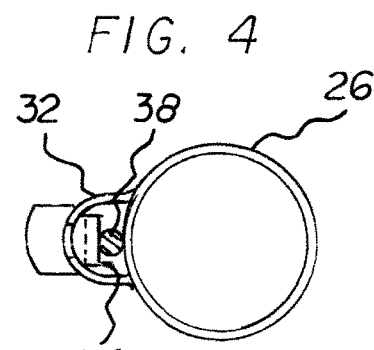
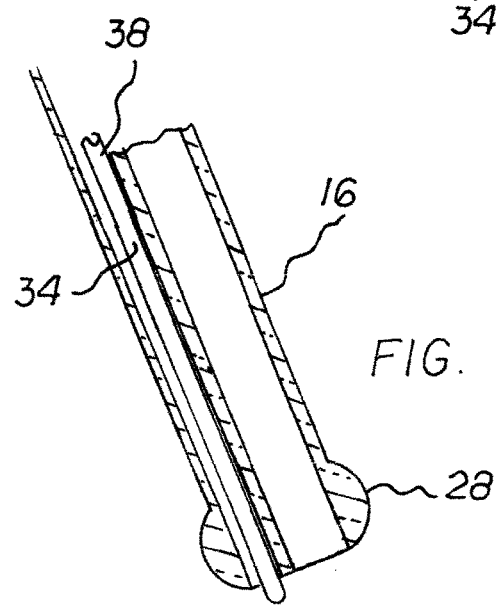

SUCTION CATHETER WITH INTUBATION GUIDE STYLET

BACKGROUND OF THE INVENTION

Field of the Invention

The present invention relates to a suction catheter with intubation guide stylet and more particularly pertains to simultaneous suctioning of the oral pharynx with placement of an intubation guide stylet which will abate foreign matter from entering the lungs of a patient. The suctioning and intubation guide stylet placement while abating being done in a safe, convenient, and economical manner.

Description of the Prior Art

The use of suction catheters with intubation guide stylet of known designs and configurations is known in the prior art. More specifically, suction catheters with intubation guide stylet of known designs and configurations previously devised and utilized for the purpose of suctioning and intubating patients are known to consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, the aforementioned patents do not describe a suction catheter with intubation guide stylet that allows simultaneous suctioning of the oral pharynx with placement of an intubation guide stylet while abating foreign matter from entering the lungs of a patient.

Therefore, it can be appreciated that there exists a continuing need for a new and improved suction catheter with intubation guide stylet which can be used for intubating a patient with an endotracheal tube while abating foreign matter from entering the lungs of a patient. The intubating and the abating being done in a safe, convenient, and economical manner. In this regard, the present invention substantially fulfills this need.

SUMMARY OF THE INVENTION

In view of the disadvantages inherent in the known types of endotracheal tube placement devices of known designs and configurations now present in the prior art, the present invention provides an improved suction catheter with intubation guide stylet. As such, the general purpose of the present invention, which will be described subsequently in greater detail, is to provide a new and improved endotracheal tube placement device and method which has all the advantages of the prior art and none of the disadvantages.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

For a better understanding of the invention, its operating advantages and the specific objects attained by its uses, reference should be made to the accompanying drawings and descriptive matter in which there is illustrated preferred embodiments of the invention.

To attain this, the present invention essentially comprises in its broad context, a suction device having an upper section with an upper end formed as a handle. The suction device also has a lower end shaped as a torus. A lateral component is integrally formed with the intubation device and extends from adjacent to the upper end and adjacent to the lower end. The lateral component has a passageway there through. The suction device and the lateral component are fabricated of a generally rigid plastic material. Next provided in this broad context is an intubation guide stylet slidably positioned in the passageway of the lateral component. The intubation guide stylet has a top positionable above the lateral component and has a bottom positionable below the lateral component. Such components are individually configured and correlated with respect to each other so as to attain the desired objective.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including such equivalent constructions insofar as they do not depart from the spirit and scope of the present invention.

It is therefore an object of the present invention to provide a new and improved suction catheter with intubation guide stylet which has all of the advantages of the prior art suction catheters with intubation guide stylet of known designs and configurations and none of the disadvantages.

It is another object of the present invention to provide a new and improved suction catheter with intubation guide stylet which may be easily and efficiently manufactured and marketed.

It is further object of the present invention to provide a new and improved suction catheter with intubation guide stylet which is of durable and reliable constructions.

An even further object of the present invention is to provide a new and improved suction catheter with intubation guide stylet which is susceptible of a low cost of manufacture with regard to both materials and labor, and which accordingly is then susceptible of low prices of sale to the consuming public, thereby making such suction catheter with intubation guide stylet economically available to the buying public.

Lastly, another object of the present invention is to provide a suction catheter with intubation guide stylet for simultaneous suctioning of the oral pharynx with placement of an intubation guide stylet while abating foreign matter from entering the lungs of a patient. The suctioning and intubation guide stylet placement while abating being done in a safe, convenient, and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a side elevational view of a suction catheter with intubation guide stylet constructed in accordance with the principles of the present invention.

FIG. 2 is an end elevational view taken along line 2-2 of FIG. 1.

FIG. 3 is a cross sectional view taken along line 3-3 of FIG. 2.

FIG. 4 is a cross sectional view taken along line 4-4 of FIG. 3.

FIG. 5 is a cross sectional view taken along line 5-5 of FIG. 2.

The same reference numerals refer to the same parts throughout the various Figures.

DESCRIPTION OF THE PREFERRED EMBODIMENT

Figures 6, 7:
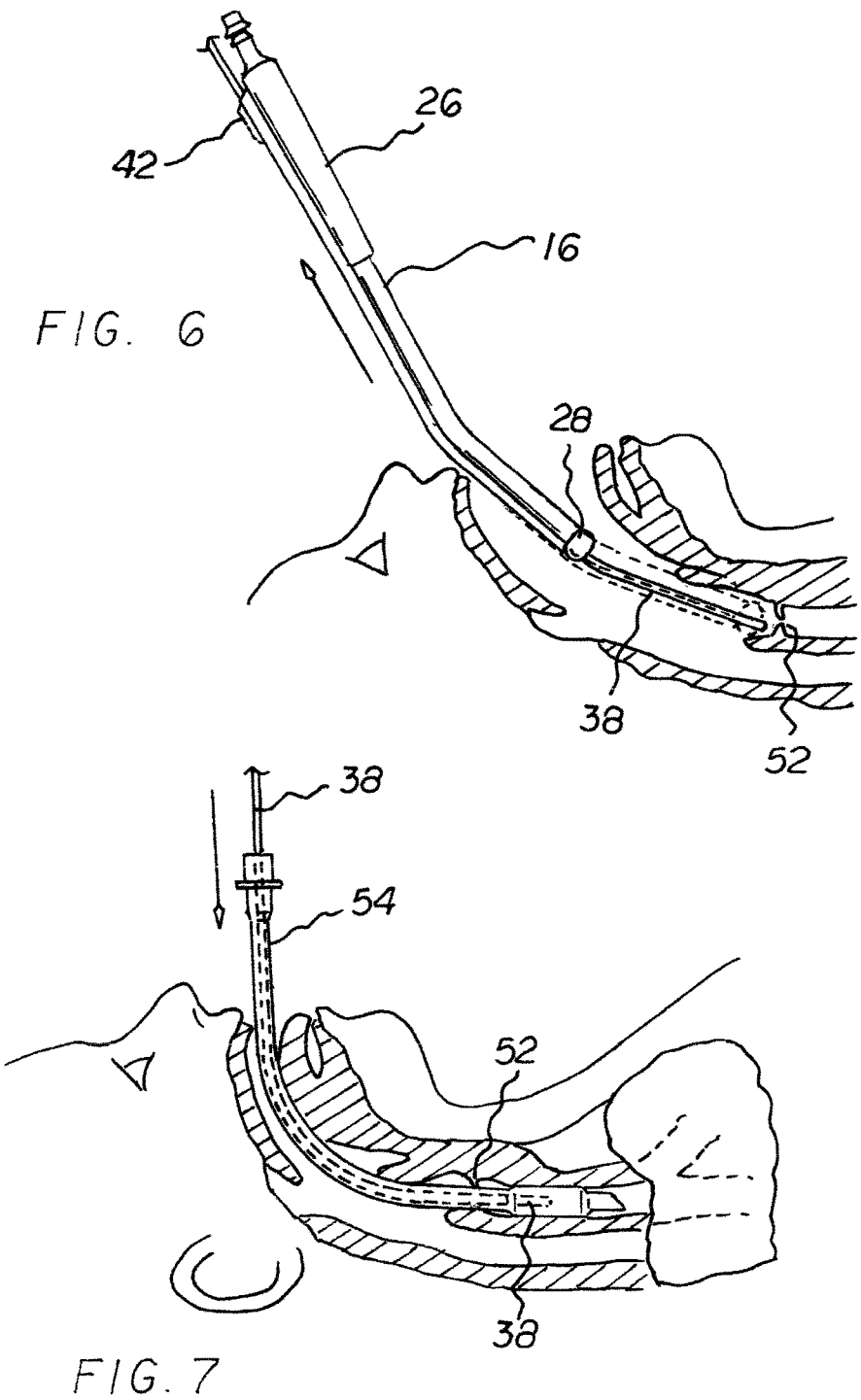
FIG. 6 is a cross sectional view of an intubation guide stylet being positioned.
FIG. 7 is a cross sectional view of an endotracheal tube being positioned.

With reference now to the drawings, and in particular to FIG. 1 thereof, the preferred embodiment of the new and improved suction catheter with intubation guide stylet embodying the principles and concepts of the present invention and generally designated by the reference numeral 10 will be described.

The present invention, the suction catheter with intubation guide stylet 10 is comprised of a plurality of components. Such components are individually configured and correlated with respect to each other so as to attain the desired objective. In their broadest context such include a suction device, a lateral component, and an intubation guide stylet.

The preferred embodiment of the suction catheter with intubation guide stylet, designated by reference numeral 10, is for simultaneous suctioning of the oral pharynx with placement of an intubation guide stylet while abating foreign matter from entering the lungs of a patient. The suctioning and intubation guide stylet placement are done in a safe, convenient, and economical matter.

From this specific standpoint, first provided is a suction device 16 having an upper section 18 and a lower section 20. The upper section is linear with a first length. The lower section is linear with a second length less than the first length. A bend of between 10 degrees and 20 degrees is provided between the first section and the second section to form an interior edge 22 and an exterior edge 24. The upper section has an upper end formed as a handle 26. The lower section has a lower end shaped as a torus 28. The suction device is fabricated of a rigid plastic material with a major passageway there through. The major passageway has a major circumference along a majority of the lengths of the upper and lower sections.

Next, a lateral component 32 is provided. The lateral component is integrally formed with the suction device. The lateral component is located along the exterior edge of the suction device and extends from adjacent the upper end of the upper section of the suction device and adjacent the lower end of the lower section of the suction device, the lateral component is fabricated of a rigid plastic material with a minor passageway 34 there through. The minor passageway has a minor circumference along its entire length. The suction device and the lateral component are positioned in the oral pharynx of a patient in advance of the vocal cords of the patient.

An intubation guide stylet 38 is next provided. The intubation guide stylet is slidably positioned in the minor passageway of the lateral component. The intubation guide stylet has a top positioned above the lateral component for manipulation by a health care provider. The intubation guide stylet has a bottom positioned at the opening of the lateral component.

Next provided is an advancement assembly 42. The advancement assembly includes an axial slot 44 formed in the lateral component adjacent to the upper end of the upper section of the suction device. A slider 46 is reciprocably secured within the axial slot. The slider has a toothed exterior 48 adapted to be reciprocated by the health care provider. The slider has a toothed interior 50 in contact with the intubation guide stylet and adapted to advance the intubation guide stylet to a location beyond the vocal cords 52 of the patient in response to movement of the toothed exterior by the health care provider.

Lastly, an endotracheal tube 54 is provided. The endotracheal tube is adapted to be slid over the intubation guide stylet after removal of the suction catheter with intubation guide stylet with the intubation guide stylet in place. Note FIG. 6. The suction catheter with intubation guide stylet has a first end and a second end separated by a suction catheter length to be positioned with the first end exterior of the patient and the second end interior of the patient beyond the vocal cords adjacent to the lungs.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A suction catheter and intubation-guide stylet comprising:
   a suction device having an upper section with an upper end formed as a handle, the suction device having a lower end shaped as a torus;
   a lateral component integrally formed with the suction device and extending from adjacent to the upper end and adjacent to the lower end, the lateral component having a passageway there through, the suction device and the lateral component being fabricated of a rigid plastic material;
   an intubation guide stylet slidably positioned in the passageway of the lateral component, the intubation guide stylet having a top positionable above the lateral component, the intubation guide stylet having a bottom positionable below the lateral component; and
   an advancement assembly including an axial slot formed in the lateral component adjacent to the upper end of upper section of the suction device, a slider reciprocably secured within the axial slot, the slider having a toothed exterior adapted to be reciprocated by a health care provider, the slider having a toothed interior in contact with the intubation guide stylet and adapted to advance the intubation guide stylet to a location beyond vocal cords of a patient in response to movement of the toothed exterior by the health care provider.

2. The system as set forth in claim 1 and further including:
   an endotracheal tube adapted to be slid over the intubation guide stylet after removal of the suction device with the intubation guide stylet in place, the endotracheal tube having a first end and a second end separated by a length, the endotracheal tube adapted to be positioned with the first end exterior of the patient and the second end interior of the patient beyond the vocal cords adjacent to lungs of the patient.

3. A suction catheter and intubation guide stylet system (10) for simultaneous suctioning of an oral pharynx with placement of an intubation guide stylet while abating foreign matter from entering lungs of a patient, comprising, in combination:
   a suction device (16) having an upper section (18) and a lower section (20), the upper section being linear with a first length, the lower section being linear with a second length less than the first length, a bend of between 10 degrees and 20 degrees between the first section and the second section to form an interior edge (22) and an exterior edge (24), the upper section having an upper end formed as a handle (26), the lower section having a lower end shaped as a torus (28), the suction device being fabricated of a rigid plastic material with a major passageway there through, the major passageway having a major circumference along a majority of the lengths of the upper and lower sections;
   a lateral component (32) integrally formed with the suction device, the lateral component located along the exterior edge of the suction device and extending from adjacent the upper end of the upper section of the suction device and adjacent the lower end of the lower section of the suction device, the lateral component being fabricated of a rigid plastic material with a minor passageway (34) there through, the minor passageway having a minor circumference along its entire length, the suction device and the lateral component adapted to be positioned in the oral pharynx of a patient in advance of vocal cords of the patient;
   an intubation guide stylet (38) slidably positioned in the minor passageway of the lateral component, the intubation guide stylet having a top positioned above the lateral component for manipulation by a health care provider, the intubation guide stylet having a bottom positioned below the lateral component;
   an advancement assembly (42) including an axial slot (44) formed in the lateral component adjacent to the upper end of the upper section of the suction device, a slider (46) reciprocably secured within the axial slot, the slider having a toothed exterior (48) adapted to be reciprocated by the health care provider, the slider having a toothed interior (50) in contact with the intubation guide stylet and adapted to advance the intubation guide stylet to a location beyond the vocal cords (52) of the patient in response to movement of the toothed exterior by the health care provider; and
   an endotracheal tube (54) adapted to be slid over the intubation guide stylet after removal of the suction device with the intubation guide stylet in place, the endotracheal tube having a first end and a second end separated by an endotracheal tube length to be positioned with the first end exterior of the patient and the second end interior of the patient beyond the vocal cords adjacent to the lungs.

\* \* \* \* \*